United States Patent [19]

Laskovics et al.

[11] Patent Number: 5,401,883
[45] Date of Patent: Mar. 28, 1995

[54] PROCESS FOR PREPARING 2,6-DI-TERTIARYBUTYL-4-MERCAPTO-PHENOL AND 4,4'-ISOPROPYLIDENEDITHIO-BIS-(2,6-DI-TERTIARYBUTYLPHENOL)

[75] Inventors: F. Mark Laskovics, Cincinnati, Ohio; Kim G. Bargeron, Midland, Mich.

[73] Assignee: Merrell Dow Pharmaceuticals Inc., Cincinnati, Ohio

[21] Appl. No.: 88,462

[22] Filed: Jul. 7, 1993

Related U.S. Application Data

[63] Continuation-in-part of Ser. No. 994,610, Dec. 17, 1992, abandoned, which is a continuation of Ser. No. 875,560, Apr. 27, 1992, abandoned, which is a continuation of Ser. No. 719,099, Jun. 21, 1991, abandoned, which is a continuation of Ser. No. 511,812, Apr. 17, 1990, abandoned, which is a continuation of Ser. No. 325,043, Mar. 13, 1989, abandoned, which is a continuation of Ser. No. 211,129, Jun. 21, 1988, abandoned, which is a continuation of Ser. No. 5,510, Jan. 20, 1987, abandoned.

[51] Int. Cl.$^6$ .......................................... C07C 319/06
[52] U.S. Cl. ............................................ 568/47; 568/62
[58] Field of Search ................................. 568/47, 62

[56] References Cited

U.S. PATENT DOCUMENTS

| | | | |
|---|---|---|---|
| 2,402,614 | 6/1946 | Farlow et al. | 260/609 |
| 2,402,686 | 6/1946 | Signaigo | 260/609 |
| 2,810,765 | 10/1957 | Neuworth et al. | 260/609 |
| 3,275,694 | 9/1966 | Hahn et al. | 260/609 |
| 3,479,407 | 11/1969 | Laufer | 260/608 |
| 3,576,883 | 4/1971 | Neuworth | 260/609 |
| 3,678,115 | 7/1972 | Fujisawa et al. | 260/609 |
| 3,718,699 | 2/1973 | Fujisawa et al. | 260/608 |
| 3,812,192 | 5/1974 | Gabler et al. | 260/608 |
| 3,952,064 | 4/1976 | Whalley | 260/608 |
| 4,734,527 | 3/1988 | Krauss | 260/609 |
| 4,772,363 | 9/1988 | VanEffen | 260/608 |

FOREIGN PATENT DOCUMENTS

| | | | |
|---|---|---|---|
| 0200212 | 11/1986 | European Pat. Off. | 260/609 |
| 163536 | 12/1979 | Japan | 260/609 |
| 9041 | 1/1980 | Japan | 260/609 |
| 17316 | 2/1980 | Japan | 260/609 |
| 549013 | 11/1985 | Spain | 260/609 |
| 1199871 | 7/1970 | United Kingdom | 260/609 |
| 1290132 | 9/1972 | United Kingdom | 260/608 |
| 1348491 | 3/1974 | United Kingdom | 260/608 |
| 1425278 | 2/1976 | United Kingdom | 260/608 |
| 1443329 | 7/1976 | United Kingdom | 260/608 |

OTHER PUBLICATIONS

Japanese Application 43 28425; Dec. 22, 1970; Derwent Abstract 52259U-E.
Chemical Abstracts 95:150171g, G. Ramos et al., 1981.
American Cyanamid Catalyst Brochure-HDS-20 catalyst, 1978.
Sulphide Catalysts, Their Properties and Applications; Weisser et al; 1973; pp. 192–193 and 278–279.
E. B. Hotelling, et al., *J. Org. Chem.* 24:1598 (1959).
Houben & Weyl, *Methoden der Organischen Chemie*, vol. 9 (1955).
T. Ohtsuka, *Catal. Rev.-Sci. Eng.*, 12(2):291 (1977).

*Primary Examiner*—Mary C. Lee
*Assistant Examiner*—Joseph K. McKane

[57] ABSTRACT

This invention relates to an improvement in a process for making 2,6-di-tertiarybutyl-4-mercaptophenol and 4,4-isopropylidenedithio-bis-(2,6-di-tertiarybutylphenol) which comprises reduction of bis (3,5-di-tertiarybutyl-4-hydroxyphenyl)polysulfide with hydrogen gas at a temperature range of from about 20° C. to about 90° C. in the presence of a catalytic amount of cobalt-molybdenum catalyst.

12 Claims, No Drawings

PROCESS FOR PREPARING 2,6-DI-TERTIARYBUTYL-4-MERCAPTOPHENOL AND 4,4'-ISOPROPYLIDENEDITHIO-BIS-(2,6-DI-TERTIARYBUTYLPHENOL)

This is a continuation-in-part of application Ser. No. 07/994,610, filed Dec. 17, 1992, now abandoned; which is a continuation of Ser. No. 07/875,560, filed Apr. 27, 1992, now abandoned; which is a continuation of Ser. No. 07/719,099, filed Jun. 21, 1991, now abandoned; which is a continuation of application Ser. No. 511,812, filed Apr. 17, 1990, now abandoned; which is a continuation of application Ser. No. 325,043, filed Mar. 13, 1989, now abandoned; which is a continuation of application Ser. No. 211,129, filed Jun. 21, 1988, now abandoned; which is a continuation of application Ser. No. 005,510, filed Jan. 20, 1987, now abandoned.

BACKGROUND OF THE INVENTION

This invention relates to a novel, improved process of making 2,6-di-tertiarybutyl-4-mercaptophenol by a cobalt-molybdenum catalyzed reduction of bis (3,5-di-tertiarybutyl-4-hydroxyphenyl)polysulfide in the presence of hydrogen gas at a temperature range of from about 20° C. to about 90° C. This mercaptophenol is an intermediate in the synthesis of 4,4'-isopropylidenedithio-bis-(2,6-di-tertiarybutylphenol) which has been disclosed in U.S. Pat. No. 3,576,883 as an effective pharmaceutical agent for the reduction of serum cholesterol. This invention further relates to a novel, improved process of making 4,4'-iso-propylidenedithio-bis-(2,6-di-tertiarybutylphenyl) by further reacting the 2,6-di-tertiarybutyl-4-mercaptophenol thus formed with acetone in the presence of acid.

DESCRIPTION OF THE BACKGROUND ART

U.S. Pat. No. 3,479,407 teaches the preparation of a mixture of bis(3,5-di-tertiarybutyl-4-hydroxyphenyl)polysulfide, comprising principally the disulfide, by a process of sulfurization of 2,6-di-tertiarybutylphenol (DTBP) with sulfur monochloride in the presence of an iodine catalyst. The polysulfide had been shown to be reduced to 2,6-di-tertiarybutyl-4-mercaptophenol by a process comprising a Zn/HCl reduction as disclosed in U.S. Pat. Nos. 3,952,064 and 3,479,407 and in Japanese Patent Application 73-28425. Condensation of the resulting mercaptophenol in the presence of acetone under acidic conditions results in the formation of 4,4'-isopropylidenedithio-bis-(2,6-di-tertiarybutylphenol), as described in U.S. Pat. No. 3,576,883. This reaction sequence is presented below.

Scheme A

1.
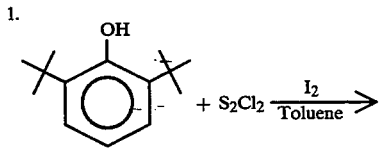

-continued
Scheme A

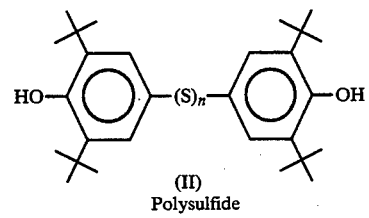

2.
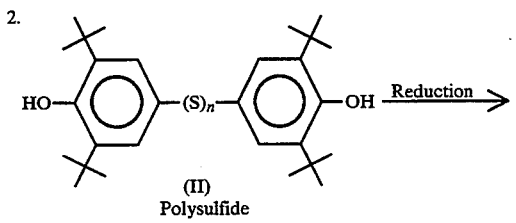

3.

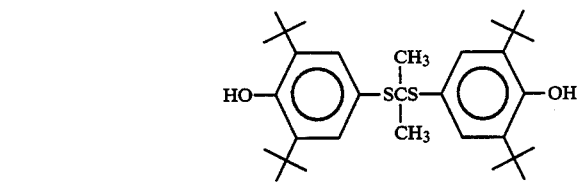

$+$ = tertiarybutyl group n = 2, 3, 4, . . .; principal product is the disulfide

SUMMARY OF THE INVENTION

The following terms are used herein as follows:
"DTBP" refers to 2,6-di-tertiarybutylphenol (I).
"Polysulfide" and "Bis(3,5-di-tertiarybutyl-4-hydroxyphenyl)polysulfide" both are used to refer to one or more species of bis(3,5-di-tertiarybutyl-4-hydroxyphenyl)polysulfide (II) including the di-, tri-, tetra-, and other higher order sulfides, and including single species as well as mixtures thereof. Typically, the Polysulfide is a mixture of two or more species with the disulfide present in amounts greater than other species.

"Mercaptophenol" refers to 2,6-di-tertiarybutyl-4-mercaptophenol (III).

"Catalytic amount" refers to that amount of a Cobalt-Molybdenum preparation which is sufficient to catalyze the reduction of Polysulfide to Mercaptophenol in the presence of Hydrogen gas. This amount may vary under particular conditions of use whereby other experimental parameters are varied including concentration of Polysulfide, absolute amount of Polysulfide, hydrogen gas pressure, temperature, residence time on the trickle-bed reactor column, and surface area of the catalyst.

"g" and "cc" refer to grams and cubic centimeters, respectively.

The novel improvement in the process of making the Mercaptophenol and 4,4'-isopropylidenedithio-bis-(2,6-di-tertiarybutylphenol) comprises a cobalt-molybdenum catalyzed hydrogenation of the Polysulfide (II) at a temperature range of from about 20° C. to about 90° C. This lower temperature range represents an improved process over the cobalt-molybdenum hydrogenation process which is performed at considerably higher temperatures, such as 160° C., to 168° C., as described by Neuworth et al. in U.S. Pat. No. 2,810,765. When conducted at higher temperatures this hydrogenation results in a significant increase of undesired by-products.

The cobalt-molybdenum reduction also represents a significant improvement over the Zn/HCl reduction described in U.S. Pat. No. 3,479,407. The Zn/HCl reduction requires a lengthy and tedious batch reduction with subsequent crystallization in order to isolate the Mercaptophenol for the condensation step to form 4,4'-isopropylidenedithio-bis-(2,6-di-tertiarybutylphenol).

When the improved process is carried out utilizing a fixed-bed reactor, it provides a streamlined, continuous-flow method for preparing the Mercaptophenol. The reaction mixture effluent can be utilized directly in the condensation step to form 4,4'-isopropylidenedithio-bis-(2,6'-ditertiary-butylphenol) without prior isolation of the Mercaptophenol.

Thus, the present improved process allows Polysulfide, which is introduced into a trickle-bed reactor containing a fixed-bed, cobalt-molybdenum catalyst in the presence of hydrogen gas at a temperature range of from about 20° C. to about 90° C., to be converted to the Mercaptophenol which is present in the reaction-mixture effluent. The effluent can then be reacted in a continuous or a batch-wise manner with acetone under acidic conditions to form 4,4'-isopropyl-idenedithio-bis-(2,6-di-tertiarybutylphenol) without prior isolation of the Mercaptophenol.

The trickle-bed reactor in which the hydrogenation takes place can comprise a jacketed pipe configured as a vertical column in which sufficient catalyst, hydrogen pressure and temperature is maintained to support the reaction. The reactor is charged with a catalytic amount of cobalt-molybdenum catalyst. The preferred cobalt-molybdenum catalyst comprises about 5% cobalt oxide and about 16% molybdenum oxide on an inert support material. Alumina is preferred as the support material. The amount of surface area provided by a particular catalyst preparation is chosen so as to provide optimum hydrogenation results. The feed solution or liquid enters the top of the column by means of a pump. Hydrogen gas is introduced into the reactor and regulated by means of a pressure regulator. The feed solution mixes with the gas and cascades through the catalyst bed with the feed solution maintaining contact with both the catalyst and the hydrogen gas throughout the reactor. The exit stream exits into a liquid level control tank in which the liquid is allowed to collect in order to provide a liquid seal thereby maintaining the gas pressure. The effluent collected in the liquid level control tank is allowed to exit in such a manner so as to maintain the level of liquid in the tank.

The Polysulfide can be prepared by sulfur monochloride sulfurization of DTBP, preferably as described in U.S. Pat. No. 3,479,407. The Polysulfide can be dissolved in any solvent in which it is soluble and which is non-reactive under the conditions set forth below. Toluene is the preferred solvent. The trickle-bed reactor can be prepared as described above and the cobalt-molybdenum catalyst can be sulfided by treating with H₂S. Hydrogen gas can then be introduced at a minimum pressure of about 600 psig to maximum pressure comprising the upper limit maintainable by the system. A hydrogen pressure of about 600 psig to about 2000 psig is preferred with about 750 psig being most preferred. The temperature is maintained from about 20° C. to about 90° C., with the preferred temperature ranging from about 50° C. to about 70° C.

The temperature range employed herein is considerably lower than that taught by the art. Thus, for example, Neuworth et al., U.S. Pat. No. 2,810,765 employs a temperature range for the hydrogenation of a polysulfide in toluene of from 160° C. to 168° C. at an average hydrogen partial pressure of 850 psig over a 20% molybdenum disulfide catalyst supported on alumina pellets.

The hydrogenation of polysulfide (II) at higher temperatures results in a substantial amount of by-products being found, such as 2,6-di-tert-butyl-4-mercapto-cyclohex1-enol (V), and/or its tautomer, 2-tert-butyl-4-mercaptophenol (VI) and 2,6-di-tert-butyl-4-tertbutyl-sulfanylphenol (VII), in addition to Mercaptophenol (III) as described in Scheme B.

However, by lowering the temperature at which the hydrogenation is conducted the formation of these undesired by-products is significantly diminished. This is neither taught nor suggested by the prior art teachings.

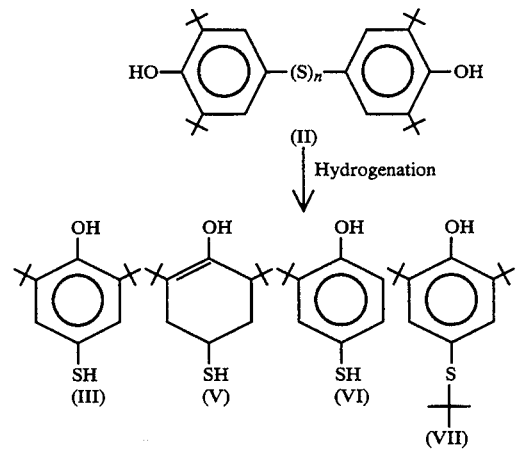

Scheme B

Thus, for example as shown in table A below, the hydrogenation of polysulfide (II) at a temperature of 120° C. results in the formation of a gas chromatographic area ratio of 0.0013 to 1 of 2,6-di-tert-butyl-4-mercapto-cyclohex-1-enol (V), 0.0026 to 1 of 2-tert-butyl-4-mercaptophenol (VI) and 0.0085 to 1 of 2,6-di-tert-butyl-4-tert-butylsulfanylphenol (VII) as undesirable by-products in the final product. Hydrogenation of polysulfide (II) at a temperature of 80° C. results in formation of a gas chromatographic area ratio of 0.0001 to 1 for by-product (V) (an overall 92% reduction), an area ratio of 0.0003 to 1 for by-product (VI) (an overall 88% reduction) and an area ratio of 0.0018 to 1 for by-product (VII) (an overall 79% reduction). These by-products are very difficult to remove from the final product.

By reducing the level of these by-products in the formation of the intermediate mercaptophenol (III), the overall efficiency of the synthesis of 4,4'-isopropylidenedithio-bis-(2,6-di-tertiarybutylphenol) (IV) is greatly enhanced.

This can be illustrated in the following table.

TABLE A

| By-product | Gas Chromatographic area at 120° C. ratio of by-products | Gas Chromatographic area at 80° C. ratio of by-products | % By-product reduction |
|---|---|---|---|
| (V) | 0.0013 | 0.0001 | 92% |
| (VI) | 0.0026 | 0.0003 | 88% |
| (VII) | 0.0085 | 0.0018 | 79% |

The in- and the out-flow rates of the solvent can be adjusted so that the liquid level in the control tank is maintained and so that the residence time of the solvent on the column is from about 3 minutes to about 60 minutes with from about 25 minutes to about 50 minutes residence time being preferred. The Polysulfide can be introduced onto the column and the resulting effluent from the trickle-bed reactor will contain the Mercaptophenol. This effluent can then be reacted further with acetone under acidic conditions to form 4,4'-isopropylidenedithio-bis-(2,6-di-tertiarybutylphenol).

The reaction conditions, in particular the amount and surface area of the cobalt-molybdenum catalyst, the concentration and absolute amount of the Polysulide used, and the residence time on the column as well as the column temperature and hydrogen pressure, can be adjusted to provide the highest yield of Mercaptophenol in the effluent. The optimum parameters can be easily determined by one skilled in the art by simple experimentation.

The following example illustrates the cobalt-molybdenum catalyzed hydrogenation of Polysulfide to make the Mercaptophenol utilizing a fixed-bed catalyst containing about 5% by weight of CoO and about 16% by weight of $MoO_3$ on an inert support material. In addition, the Mercaptophenol thus formed is converted to 4,4'-isopropylidenedithio-bis-(2,6-di-tertiarybutylphenol) by treating the reaction mixture with acetone under acidic conditions.

EXPERIMENTAL RESULTS

Example 1

High Temperature Hydrogenation

The trickle-bed reactor (1-inch diameter) was loaded with 67 g (80 cc) of ¼ inch ceramic packing, followed by 244 g (346 cc) of Co-Mo catalyst consisting of 5.0% by weight of CoO and 16.2% by weight of $MoO_3$ on approximately ⅛ inch × 1/16 inch elliptical ribbed alumina (American Cyanamid Trilobe ® HDS-20-1.6), followed by 43 g.(50 cc) of ¼ inch ceramic packing. The cobalt-molybdenum catalyst was sulfided by purging the reactor with nitrogen at room temperature, warming to 150° C., pressurizing to 100 psig nitrogen, and treating with 30 g $H_2S$ over an hour period. Toluene was used as the liquid seal. The column was maintained at 100° C. and 750 psig hydrogen gas.

A toluene solution containing Polysulfide produced by the sulfurization of DTBP, as described in U.S. Pat. No. 3,479,407, was applied to the trickle-bed reactor with a feed flow rate of 464 cc/hour. This flow rate provided a residence time of the substrate on the catalyst of about 9 minutes. The Polysulfide was almost completely reduced to the corresponding Mercaptophenol as indicated by High Performance Liquid Chromatography (HPLC) of the reactor effluent.

The Mercaptophenol was further reacted to form 4,4'-isopropylidenedithio-bis-(2,6-di-tertiarybutylphenol) by reacting 500.7 g of effluent from the trickle-bed reactor (containing an estimated 680 millimoles of Mercaptophenol) with 65.6 g (1.26 moles) of acetone, followed by 7.7 g (0.21 moles) of HCl (gas). After reacting at 20° C. for 3 hours, the reaction mixture was quenched with 100 cc of water. After stirring for 15 minutes, the layers were permitted to separate, and the bottom water layer was removed and discarded. The organic solvent was removed under reduced pressure and the residue was recrystallized three times from 90% ethanol/water yielding 4,4'-isopropylidenedithio-bis-(2,6-di-tertiarybutylphenol) with a melting point of 124.5° C. to 128° C.

Example 2

Low Temperature Hydrogenation

Pack a six-inch by twenty-foot long trickle-bed reactor, having a packed section of 13.1 feet, with 90 pounds of Co-Mo catalyst consisting of 4.5% by weight of CoO and 15.5% by weight of $MoO_3$ on approximately 1/8 inch × 1/16 inch elliptical ribbed alumina (Criterion Catalysts Trilobe ® HDS-22-1.6). ¼ inch ceramic saddle packing is used for support at the bottom and to aid in liquid distribution at the top. The cobalt-molybdenum catalyst is sulfided by purging the reactor with nitrogen at room temperature, warming to 140° C. to 160° C., pressurizing to 100 psig nitrogen, and treating with hydrogen sulfide until the entire catalyst bed is sulfided. Toluene is used as the liquid seal. Hydrogen is applied to the reactor at 750–900 psi. The column temperature is maintained at 50° C. to 70° C.

A toluene solution containing Polysulfide (II) produced by the sulfurization of DTBP, as described in U.S. Pat. No. 3,479,407, is applied to the trickle-bed reactor at a feed flow rate of about 36.8 liters/hr. This flow rate provides a residence time of the substrate on the catalyst of about 33 minutes. The Polysulfide is almost completely reduced to the corresponding Mercaptophenol (III) as indicated by High Performance Liquid Chromatography (HPLC) of the reactor effluent.

The Mercaptophenol (III) is reacted with acetone in the presence of HCl (gas) in a manner analogous to that described in example 1 to form the 4,4'-isopropylidenedithio-bis-(2,6-di-tertiarybutylphenol).

It is understood that the foregoing detailed description is given merely by way of illustration and that many modifications may be made therein without departing from the spirit of scope of the present invention.

What is claimed is:-

1. A process for making a compound of the formula:

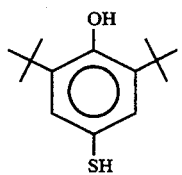

which is substantially free of reaction by-products comprising reducing bis(3,5-di-tertiarybutyl-4-hydroxyphenyl)polysulfide with hydrogen gas in the presence of a catalytic amount of a sulfided cobalt-molybdenum catalyst further comprising from about 4.5% to about 5.0% cobalt oxide and from about 15.5% to about 16.2% molybdenum trioxide, wherein the temperature of the reaction is from about 20° C. to about 90° C.

2. A process for making a compound of the formula:

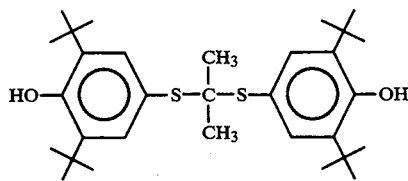

which is substantially free of reaction by-products comprising reducing bis(3,5-di-tertiarybutyl-4-hydroxyphenyl)polysulfide with hydrogen gas in the presence of a catalytic amount of cobalt-molybdenum catalyst further comprising from about 4.5% to about 5.0% cobalt oxide and from about 15.5% to about 16.2% molybdenum trioxide, to get a mercaptophenol reaction product wherein the temperature of the reaction is from about 20° C. to about 90° C., and further reacting the reaction product with acetone under acidic conditions.

3. The process of claim 1 wherein the catalyst comprises about 4.5% by weight of cobalt oxide and about 15.5% by weight of molybdenum oxide on a solid inert support.

4. The process of claim 1 wherein the reduction is carried out at a temperature from about 50° C. to about 70° C.

5. The process of claim 1 wherein the hydrogen gas is maintained at a pressure of about 600 psig to about 2000 psig.

6. The process of claim 1 wherein the reduction is carried out in a continuous flow manner by passing a solution of bis(3,5-di-tertiarybutyl-4-hydroxyphenyl)-polysulfide in an inert solvent through a fixed bed of the catalyst.

7. The process of claim 6 wherein the 2,6-di-tertiarybutyl-4-mercaptophenol is continuously withdrawn from the effluent of the fixed catalyst bed.

8. The process of claim 2 wherein the catalyst comprises about 4.5% by weight of cobalt oxide and about 15.5% by weight of molybdenum oxide on a solid inert support.

9. The process of claim 2 wherein the reduction is carried out at a temperature from about 50° C. to about 70° C.

10. The process of claim 2 wherein the hydrogen gas is maintained at a pressure of about 600 psig to about 2000 psig.

11. The process of claim 2 wherein the reduction is carried out in a continuous flow manner by passing a solution of bis(3,5-di-tertiarybutyl-4-hydroxyphenyl)-polysulfide in an inert solvent through a fixed bed of the catalyst.

12. The process of claim 11 wherein the 2,6-di-tertiarybutyl-4-mercaptophenol is continuously withdrawn from the effluent of the fixed catalyst bed is reacted directly with acetone in the presence of acid.

* * * * *